United States Patent
Shute et al.

(10) Patent No.: US 11,850,087 B2
(45) Date of Patent: Dec. 26, 2023

(54) HEART SOUND SENSING HEADGEAR

(71) Applicant: Cardiac Pacemakers, Inc., St. Paul, MN (US)

(72) Inventors: Jonathan Bennett Shute, Minnetonka, MN (US); Rezwan Ahmed, Arden Hills, MN (US); Bin Mi, Arden Hills, MN (US); Krzysztof Z. Siejko, Maple Grove, MN (US); Pramodsingh Hirasingh Thakur, Woodbury, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 148 days.

(21) Appl. No.: 16/386,611

(22) Filed: Apr. 17, 2019

(65) Prior Publication Data
US 2019/0343480 A1   Nov. 14, 2019

Related U.S. Application Data

(60) Provisional application No. 62/668,630, filed on May 8, 2018.

(51) Int. Cl.
*A61B 7/02* (2006.01)
*A61B 5/00* (2006.01)
(Continued)

(52) U.S. Cl.
CPC .......... *A61B 7/026* (2013.01); *A61B 5/0051* (2013.01); *A61B 5/349* (2021.01); *A61B 5/6803* (2013.01);
(Continued)

(58) Field of Classification Search
CPC .. A61B 7/026; A61B 7/04; A61B 7/00; A61B 5/0051; A61B 5/6803;
(Continued)

(56) References Cited

U.S. PATENT DOCUMENTS 5,649,535 A * 7/1997 Voith ................ A61B 5/02233
600/493
7,682,316 B2   3/2010 Anderson et al.
(Continued)

FOREIGN PATENT DOCUMENTS

WO   WO-2004032741 A1   4/2004
WO   WO-2015177787 A1   11/2015

OTHER PUBLICATIONS

Kusche, Roman, et al. "An in-ear pulse wave velocity measurement system using heart sounds as time reference." Current Directions in Biomedical Engineering 1.1 (2015): 366-370. Relates to a pulse wave measurement system using pressure waves sensed from the ear canal. (Year: 2015).*

(Continued)

*Primary Examiner* — Gary Jackson
*Assistant Examiner* — Alexander M Eisenberg
(74) *Attorney, Agent, or Firm* — Schwegman Lundberg & Woessner, P.A.

(57) ABSTRACT

Systems and methods for detecting heart sound information from a subject's head are described. A system embodiment includes a headgear to be worn on the subject's head, and first and second sensors to sense respectively first and second physiologic signals each representing vibration, motion, or displacement conducted through patient body tissue. The sensed physiologic signals contain heart sound information. At least one of the first or the second sensor is included in the headgear, and placed at a head location to sense a physiologic signal indicative of heart sounds. The system includes a processor to generate a composite signal using the sensed first and second physiologic signals. The system may generate a heart sound metric using the composite signal, and detect a cardiac event such as an arrhythmia or worsening heart failure.

20 Claims, 8 Drawing Sheets

(51) Int. Cl.
*A61B 7/04* (2006.01)
*A61B 5/349* (2021.01)
*A61B 5/0205* (2006.01)
*A61N 1/362* (2006.01)
*A61B 5/1455* (2006.01)

(52) U.S. Cl.
CPC .............. *A61B 5/6817* (2013.01); *A61B 7/04* (2013.01); *A61B 5/02055* (2013.01); *A61B 5/1455* (2013.01); *A61B 5/486* (2013.01); *A61B 2562/0204* (2013.01); *A61N 1/362* (2013.01)

(58) Field of Classification Search
CPC ..... A61B 5/6817; A61B 5/0452; A61B 5/486; A61B 5/02055; A61B 5/7203; A61B 5/1102; A61B 5/1455; A61B 2562/0204; A61N 1/362
See application file for complete search history.

(56) References Cited

U.S. PATENT DOCUMENTS

| | | | |
|---|---|---|---|
| 7,853,327 | B2 | 12/2010 | Patangay et al. |
| 2003/0220584 | A1* | 11/2003 | Honeyager .............. A61B 7/04 600/559 |
| 2004/0242976 | A1* | 12/2004 | Abreu .................. A61B 5/4064 600/315 |
| 2006/0253300 | A1 | 11/2006 | Somberg et al. |
| 2008/0146890 | A1* | 6/2008 | LeBoeuf .................. A61B 5/01 600/300 |
| 2009/0024004 | A1 | 1/2009 | Yang |
| 2010/0063840 | A1 | 3/2010 | Hoyme et al. |
| 2010/0217098 | A1* | 8/2010 | LeBoeuf ............ A61B 5/02433 600/301 |
| 2011/0125060 | A1* | 5/2011 | Telfort .................. A61B 7/003 600/586 |
| 2011/0144457 | A1* | 6/2011 | Coulon ................ A61B 5/0022 600/301 |
| 2011/0213271 | A1* | 9/2011 | Telfort ...................... A61B 7/04 600/586 |
| 2013/0197597 | A1* | 8/2013 | Anderson .............. A61B 5/026 600/509 |
| 2014/0051939 | A1* | 2/2014 | Messerschmidt .. A61B 5/02444 600/301 |
| 2014/0194702 | A1* | 7/2014 | Tran ...................... A61B 5/1112 600/301 |
| 2014/0288447 | A1* | 9/2014 | Luna .................... A61B 5/6838 600/508 |
| 2014/0343438 | A1* | 11/2014 | Sweeney .............. A61B 5/0809 600/484 |
| 2014/0378849 | A1* | 12/2014 | Krimsky .............. A61B 5/0205 600/513 |
| 2015/0119758 | A1* | 4/2015 | Rogers ................. A61B 5/7203 600/586 |
| 2016/0249839 | A1* | 9/2016 | Wong .................... A61B 5/6826 600/323 |
| 2017/0041699 | A1* | 2/2017 | Mackellar ............ A61B 5/0476 |
| 2017/0070834 | A1 | 3/2017 | Ben-ami et al. |
| 2017/0095160 | A1 | 4/2017 | Thakur et al. |
| 2017/0181708 | A1* | 6/2017 | Orron ................ A61B 5/02438 |
| 2017/0188868 | A1* | 7/2017 | Kale ........................ A61B 7/04 |
| 2018/0000363 | A1* | 1/2018 | Pekonen .............. A61B 5/6843 |
| 2018/0000425 | A1* | 1/2018 | Hernacki ............. A61B 5/4812 |
| 2018/0116597 | A1* | 5/2018 | Yu ........................ A61B 5/0064 |
| 2019/0045298 | A1* | 2/2019 | Klemme ............. G10L 21/0208 |
| 2019/0167200 | A1* | 6/2019 | Jang ...................... A61B 5/7221 |

OTHER PUBLICATIONS

Giovangrandi, Laurent, et al., "Ballistocardiography—A Method Worth Revisiting", NIH PA Author Manuscript, Conf Proc IEEE Eng Med Biol Soc. 2011; 2011: 4279-4282. doi:10.1109/IEMBS.2011.6091062.

* cited by examiner

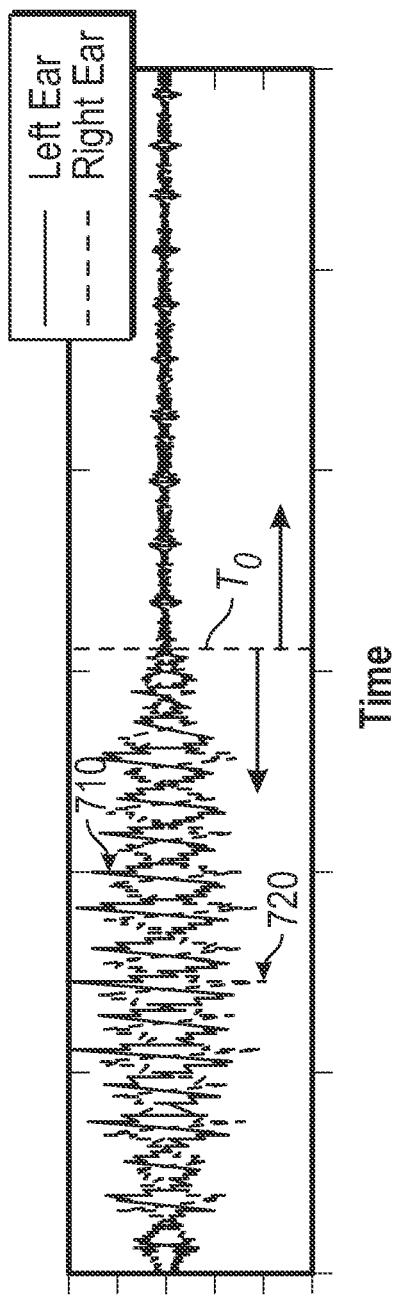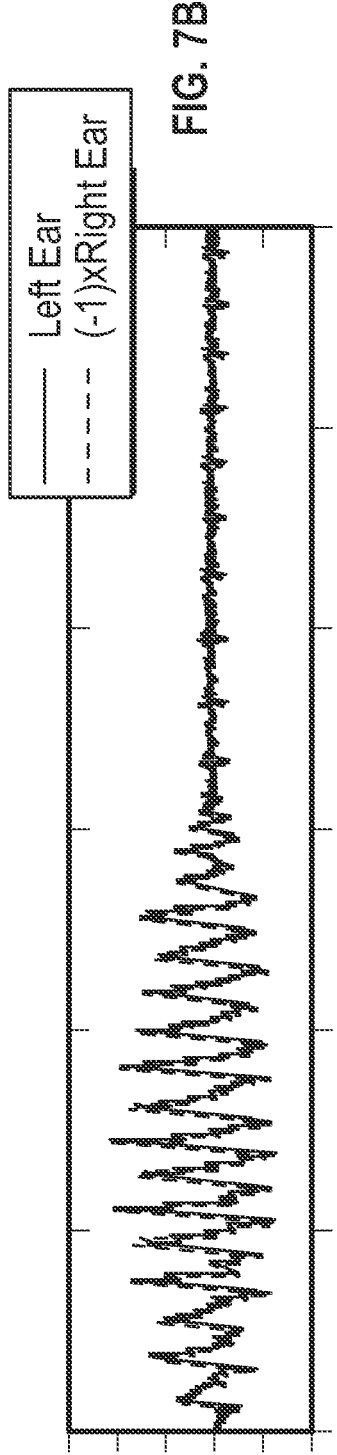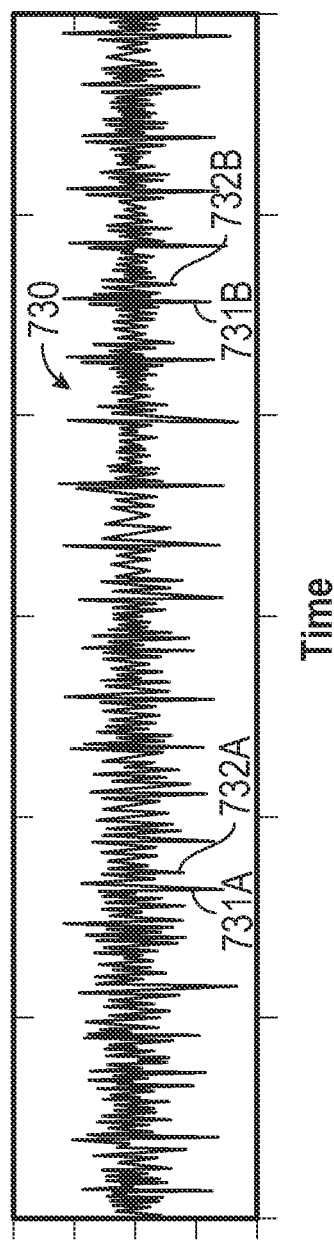

HEART SOUND SENSING HEADGEAR

CLAIM OF PRIORITY

This application claims the benefit of priority under 35 U.S.C. § 119(e) of U.S. Provisional Patent Application Ser. No. 62/668,630, filed on May 8, 2018, which is herein incorporated by reference in its entirety.

TECHNICAL FIELD

This document relates generally to medical devices, and more particularly, to systems and methods for detecting heart sound information from a subject's head.

BACKGROUND

Heart sounds are associated with mechanical vibration of a heart and blood flow through the heart. Heart sounds recur with each cardiac cycle and are separated and classified according to the activity associated with the vibration. Typically, heart sounds sensed from a subject may include several components within a cardiac cycle, including a first (S1), a second (S2), a third (S3), or a fourth (S4) heart sound. S1 is associated with the vibrational sound made by the heart during tensing of the mitral valve. S2 is produced by closure of the aortic and pulmonary valves, and marks the beginning of diastole. S3 is an early diastolic sound corresponding to passive ventricular filling during diastole, when the blood rushes into the ventricles. S4 is a late diastolic sound corresponding to active ventricular filling when the atria contract and push the blood into the ventricles. In a healthy subject, S3 is usually faint and S4 is rarely audible. However, a pathologic S3 or S4 may be higher pitched and louder.

Heart sounds have been used to assess cardiac systolic and diastolic functions. Systole is the contraction or a period of contraction of the heart that causes blood to be forced out of the heart such as the ventricles and into the aorta and pulmonary artery. Diastole is the relaxation or a period of relaxation of the heart during which the blood flows back into the heart such as the ventricles. Patients with cardiac diseases may have deteriorated systolic or diastolic functions. For example, congestive heart failure (CHF) occurs when the heart is unable to supply enough blood to maintain a healthy physiologic state.

Implantable medical devices (IMDs) have been used to monitor patients with cardiac disease, such as to detect cardiac events leading to worsening heart failure (WHF). An IMD may sense physiologic signals from a patient, and deliver electrostimulation therapy to improve cardiac performance in CHF patients. Frequent patient monitoring via an IMD may help identify patients having an elevated risk of developing future heart failure events, ensure timely treatment, reduce heart failure hospitalization, improve patient outcome, and reduce healthcare cost.

SUMMARY

An ambulatory medical device (AMD), such as an implantable medical device (IMD), a subcutaneous medical device, a wearable medical device, or other external medical device, may be used to monitor cardiac patient. An AMD may sense electrical or mechanical activities of the heart via sensing electrodes and/or physiologic sensors, and detect WHF. An IMD may include a pulse generator capable of generating and delivering electrostimulation to the heart or other excitable tissue (e.g., neural targets) to restore or improve cardiac performance in a CHF patient, or to treat abnormal cardiac rhythms. Detection of the WHF event may trigger the delivery of an electrostimulation therapy, such as a resynchronization therapy (CRT) to correct cardiac dyssynchrony.

An IMD may detect a WHF event using heart sounds detected from a patient. For example, some heart failure patients have fluid accumulation in the lungs that may cause elevated ventricular filling pressure and diastolic dysfunction, which may result in pathologically louder S3. Forceful atrial contraction to overcome an abnormally stiff ventricle in a heart failure patient may produce profound S4. Therefore, monitoring heart sounds such as S3 or S4 may be helpful in evaluating patient diastolic dysfunction, detecting a WHF event, or assessing patient risk of developing future WHF.

Conventional ambulatory heart sounds detection involves placing a sensor at an epicutaneous or a subcatenous location near the heart. For example, a heart sound sensor may be included within an IMD for subcutaneous implantation, or associated with an implantable lead for epicardial or endocardial placement. However, transcutaneous heart sound sensors may not be feasible for some patients, such as those not indicated for an IMD but need non-invasive ambulatory cardiac monitoring due to their cardiac risks. Compared to implantable sensors, the noninvasive heart sound sensors may be susceptible to various noises, motion artifacts, and physical activity interferences, among others. Detection of heart sounds may also be challenging at higher heart rate or during cardiac electrostimulation. For example, because S3 and S4 generally have relatively weaker signal intensity and lower frequency than S1 or S2, detection of S3 and S4 can be challenging.

Ballistocardiography (BCG) is a non-invasive method to detect cardiac and cardiovascular-related mechanical motions. The BCG assess ballistic forces on the heart (cardiac contractions and associated blood flow) by measuring body motion generated by the ejection of the blood at each cardiac cycle. Because the BCG is a whole-body reaction (e.g., displacement, velocity, or acceleration) resulting from cardiac ejection of blood, it effectually integrates multiple forces related to movements of blood inside the heart, inside the arteries (primarily the aorta), and movement of the heart itself. The complex origin and various confounding factors may limit the application of BCG in cardiovascular diagnostics. The force-integration effect of the BCG may serve as a low-pass filter that may attenuate or distort certain heart sound components having relatively higher center frequencies, such as S1 and S2.

For at least the foregoing reasons, the present inventors have recognized that there remains a need of systems and methods for ambulatory and non-invasive detection of heart sounds, and detection or prediction of potential cardiac events such as cardiac arrhythmias or worsening heart failure using the heart sound information. The present document discusses, among other things, systems, apparatus, and methods for sensing a physiologic signal from a head location of a subject, detecting heart sound information from the physiologic signal, and generating cardiac diagnostics using the detected heart sound information. A system embodiment includes a headgear to be worn on the subject's head, and first and second sensors to sense respectively first and second physiologic signals each representing vibration, motion, or displacement conducted through body tissue. The sensed physiologic signals contain heart sound information. At least one of the first or the second sensor is included in the headgear, and placed at a head location to sense a physiologic signal indicative of heart sounds. The system includes a processor to generate a composite signal using the sensed first and second physiologic signals. The system may generate a heart sound metric using the composite signal, and detect a cardiac event such as an arrhythmia or worsening heart failure.

Example 1 is a system for sensing heart sounds in a subject. The system comprises first and second sensors each configured to sense respectively first and second physiologic signals indicative of heart sounds, and a processor that may be configured to generate a composite signal using the sensed first and second physiologic signals, and to generate a heart sound metric using the composite signal.

In Example 2, the subject matter of Example 1 optionally includes the first and second sensors that are configured to sense the respectively first and second physiologic signals from different body locations.

In Example 3, the subject matter of any of Examples 1 or 2 optionally includes a headgear configured to be adapted to a head of the subject, the headgear including at least one of the first or the second sensor to be placed at a head location of the subject to sense at least one of the first or the second physiologic signal indicative of heart sounds.

In Example 4, the subject matter of Example 3 optionally includes the headgear that may include an earpiece device configured to be positioned at an outer ear portion of the subject, the earpiece device including the at least one of the first or the second sensor to sense a physiologic signal indicative of heart sounds from the outer ear portion of the subject.

In Example 5, the subject matter of Example 4 optionally includes the earpiece device configured to be removably affixed within a portion of an auditory canal.

In Example 6, the subject matter of any one or more of Examples 4-5 optionally includes the headgear that may include first and second earpiece devices. The first earpiece device includes the first sensor configured to sense the first physiologic signal from an outer ear portion of one ear of the subject, and the second earpiece device includes the second sensor configured to sense the second physiologic signal from an outer ear portion of the other ear of the subject.

In Example 7, the subject matter of any one or more of Examples 3-6 optionally includes the headgear that may include a temple-piece configured to be positioned at a temple region of the subject. The temple-piece includes the first or the second sensor to sense a physiologic signal indicative of heart sounds from the temple region of the subject.

In Example 8, the subject matter of Example 7 optionally includes the headgear that may include first and second temple-pieces. The first temple-piece includes the first sensor configured to sense the first physiologic signal from one temple the subject. The second temple-piece includes the second sensor configured to sense the second physiologic signal from the other temple of the subject.

In Example 9, the subject matter of any one or more of Examples 3-8 optionally includes the headgear that may include a brow-piece configured to be positioned at a forehead region of the subject. The brow-piece includes the first or the second sensor to sense a physiologic signal indicative of heart sounds from the forehead region of the subject.

In Example 10, the subject matter of any one or more of Examples 1-9 optionally includes an accelerometer included in the headgear. The accelerometer is configured to sense motion, vibration, or displacement conducted through body tissue.

In Example 11, the subject matter of any one or more of Examples 1-10 optionally includes the processor configured to identify a first motion interference component from the first physiologic signal and a second motion interference component from the second physiologic signal, the first and second motion interference components each indicative of physical activity. The processor may generate the composite signal by filtering the sensed first or second physiologic signal to remove or attenuate the respective motion interference component.

In Example 12, the subject matter of Example 11 optionally includes the processor that may include a filter configured to adaptively filter the first sensed signal using characteristics of the second sensed signal. The processor may be configured to generate the composite signal using the adaptively filtered first physiologic signal indicative of heart sounds.

In Example 13, the subject matter of any one or more of Examples 11-12 optionally includes the processor that may be configured to detect a phase relationship between the first and second motion interference components, and filter the sensed first or second physiologic signal using the detected phase relationship.

In Example 14, the subject matter of Example 13 optionally includes the processor that may be configured to detect the motion interference components of the sensed first and second physiologic signals being out of phase. The processor may be configured to generate the composite signal by adding the second physiologic signal and the first physiologic signal to remove or attenuate the motion interference from the first physiologic signal.

In Example 15, the subject matter of any one or more of Examples 1-14 optionally includes an implantable device that includes the processor and the second sensor, the implantable device configured to be communicatively coupled to the first sensor.

Example 16 is a method of sensing heart sounds in a subject using first and second sensors. The method comprises steps of sensing a first physiologic signal indicative of heart sounds via the first sensor from a head location of the subject; sensing a second physiologic signal indicative of heart sounds via a second sensor from a body location different from the head location to sense the first physiologic signal; generating, via a processor circuit, a composite signal using the sensed first and second physiologic signals; and generating a heart sound metric using the composite signal.

In Example 17, the subject matter of Example 16 optionally includes steps of adapting a headgear to a head of the subject, the headgear including at least the first sensor configured to sense the physiologic signal indicative of heart sounds; providing an implantable device configured to communicate with the headgear, the implantable device includes the second sensor and the processor circuit; establishing a communication between the implantable device and the headgear; and transmitting information including the physiologic signal indicative of heart sounds between the headgear to the implantable device.

In Example 18, the subject matter of Example 17 optionally includes positioning at least one earpiece device at an outer ear portion of the subject, and sensing from the outer ear portion of the subject a physiologic signal indicative of heart sounds.

In Example 19, the subject matter of Example 17 optionally includes sensing the first physiologic signal from the outer ear portion of one ear using the first sensor included in a first earpiece device; and sensing the second physiologic signal from the outer ear portion of the other ear using the second sensor included in a second earpiece device. The first and second earpiece devices may be included in the headgear.

In Example 20, the subject matter of Example 19 optionally includes identifying, from the first and second physiologic signals, respective first and second motion interference components indicative of physical activity, and detecting a phase relationship between the first and second motion interference components. The composite signal may be generated by filtering the sensed first or second physiologic signal to remove or attenuate the respective motion interference component using the detected phase relationship.

In Example 21, the subject matter of Example 20 optionally includes the detected phase relationship indicating an out-of-phase relationship between the first and second motion interference components. The composite signal may be generated by adding the second physiologic signal and the first physiologic signal to remove or attenuate the motion interference from the first physiologic signal, in response to the detected out-of-phase relationship.

In Example 22, the subject matter of Example 17 optionally includes sensing the first physiologic signal from a temple region of the subject using a template-piece, or sensing the first physiologic signal from a forehead region of the subject using a brow-piece. The one or more of a temple-piece or a brow-piece may be included in the headgear.

In Example 23, the subject matter of Example 16 optionally includes detecting worsening heart failure using the generated heart sound metric.

Example 24 is a system for sensing heart sounds in a subject. The system comprises first and second sensors each configured to sense respectively first and second physiologic signals indicative of heart sounds, a headgear configured to be adapted to a head of the subject, such as worn on the subject's head, and a processor. The headgear includes at least one of the first or the second sensor to be placed at a head location of the subject to sense at least one of the first or the second physiologic signal indicative of heart sounds. The processor may be configured to generate a composite signal using the sensed first and second physiologic signals, and to generate a heart sound metric using the composite signal.

Example 25 is a method of sensing heart sounds in a subject using a headgear adaptable to a head of the subject, such as wearable on the subject's head, where the headgear may include at least a first sensor configured to sense a physiologic signal indicative of heart sounds. The method comprises steps of adapting the headgear to a head of the subject, such as placing the headgear on the subject's head; sensing a first physiologic signal indicative of heart sounds via at least the first sensor from a head location of the subject; sensing a second physiologic signal indicative of heart sounds via a second sensor from a body location different from the head location to sense the first physiologic signal; generating, via a processor circuit, a composite signal using the sensed first and second physiologic signals; and generating a heart sound metric using the composite signal.

The systems, devices, and methods discussed in this document may improve the medical technology of ambulatory heart sound and cardiac event detection, such as detection of WHF or cardiac arrhythmia. Compared to conventional non-invasive heart sound detection methodology such as the BCG that may attenuate or distort some heart sound components, the present system and devices detects heart sound information using a headgear-based sensor, which preserves higher frequency components generated by the cardiac contraction. This is advantageous as it improves the accuracy of detection and characterization of certain heart sound components such as S1 and S2. The systems and methods discussed herein also algorithmically improve heart sound signal quality through active noise and motion interference cancellation. As such, the systems and methods discussed herein enhances the performance and functionality of an ambulatory medical device for detecting various cardiac events, yet at little to no additional cost compared to conventional cardiac event monitoring systems and devices. Such improvement in system performance and functionality can reduce healthcare costs associated with HF management and hospitalization.

Additionally, the systems, devices, and methods discussed in this document may also allow for more efficient device memory usage, such as by storing heart sound metrics that are clinically relevant to WHF detection. As fewer false positive detections of WHF events are provided, device battery life can be extended; fewer unnecessary drugs and procedures may be scheduled, prescribed, or provided. Therapy titration, such as electrostimulation parameter adjustment, based on heart sound metrics may not only improve therapy efficacy and patient outcome, but may also save device power. As such, overall system cost savings may be realized.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 7A-7C are graphs illustrating, by way of example and not limitation, physiologic signals recorded by two earpiece devices such as the earpiece device as illustrated in FIG. 3.

DETAILED DESCRIPTION

Disclosed herein are systems, devices, and methods for sensing heart sound information from a head location of a subject, and generating a diagnostic using the sensed physiologic signal. An embodiment of the system may include a headgear wearable on the subject's head, and first and second sensors to sense respectively first and second physiologic signals each representing vibration, motion, or displacement conducted through body tissue. The sensed physiologic signals contain heart sound information. At least one of the first or the second sensor may be included in or associated with the headgear, and placed at a head location to sense information about heart sounds. The system may generate a heart sound metric using the composite signal, and detect a cardiac event such as an arrhythmia or worsening heart failure. The system may deliver a therapy in response to the detected cardiac event.

Figure 1:
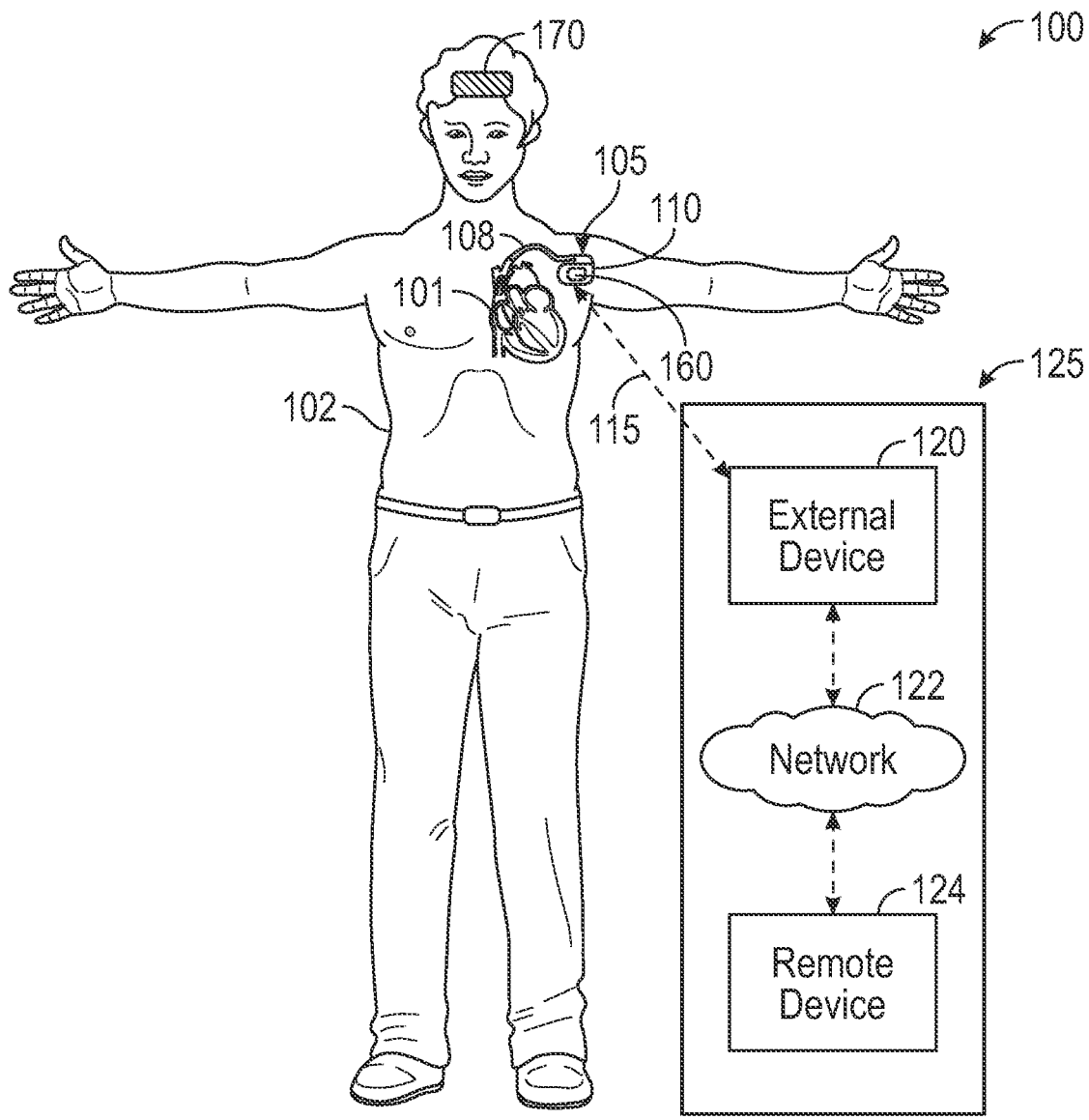
FIG. 1 illustrates generally an example of a patient management system and portions of an environment in which the system may operate.

FIG. 1 illustrates generally an example of a patient management system 100 and portions of an environment in which the system 100 may operate. The patient management system 100 may include an ambulatory system 105 associated with a patient 102, an external system 125, and a telemetry link 115 providing for communication between the ambulatory system 105 and the external system 125. In certain examples, the patient management system 100 may be configured as a heart failure management system to perform a range of acts including, for example, monitoring patient heart failure status, generating an alert of patient worsening heart failure (WHF), delivering a therapy or adjusting an existing therapy to treat heart failure or to alleviate heart failure comorbidities, or providing feedback on therapy efficacy, such as patient physiologic responses to a therapy, to a system user such as a clinician.

The ambulatory system 105 may include an ambulatory medical device (AMD) 110 and a therapy delivery system such as a lead system 108. The AMD 110 may include an implantable device that may be implanted within the body 102 and coupled to a heart 101 via the lead system 108. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, or external monitoring or therapeutic medical devices such as automatic external defibrillators (AEDs) or Holter monitors; wearable medical devices such as patch-based devices, smart watches, or smart accessories; or a bedside monitor.

By way of example, the AMD 110 may be coupled to the lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined based on the patient need and the capability of the AMD 110. The lead system 108 and the associated electrodes may deliver therapy to treat cardiac or pulmonary diseases. The therapies may include pacing, cardioversion, defibrillation, neuromodulation, drug therapies, or biological therapies, among other types of therapies. In an example, the electrodes on the lead system 108 may be positioned inside or on a surface of at least a portion of the heart, such as a right atrium (RA), a right ventricle (RV), a left atrium (LA), a left ventricle (LV), or any tissue between or near the heart portions. In an example, the lead system 108 and the associated electrodes may be implanted subcutaneously or wearable on the patient body. The associated electrodes on the lead system 108 may be positioned at the patient's thorax or abdomen to sense intrinsic physiologic signals indicative of cardiac or pulmonary activities, or physiologic responses to diagnostic or therapeutic stimulations to a target tissue. In certain examples, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may include a hermetically sealed can that houses one or more of a sensing circuit, a control circuit, a communication circuit, and a battery, among other components. The sensing circuit may sense a physiologic signal, such as by using a physiologic sensor or the electrodes associated with the lead system 108. Examples of the physiologic signal may include one or more of electrocardiogram, intracardiac electrogram, heart rate, heart rate variability, thoracic impedance, cardiac impedance, arterial pressure, pulmonary artery pressure, left atrial pressure, RV pressure, LV coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature, among others. In some examples, the AMD 110 may be coupled to a data storage device, such as an electronic medical record (EMR) system, and receive physiologic data from the data storage device.

The patient management system 100 may include a cardiac monitor circuit 160 configured to monitor patient cardiac status. The cardiac monitor circuit 160 may be substantially enclosed within the AMD 110 as illustrated in FIG. 1, or alternatively may be substantially included in the external system 125, or distributed between the ambulatory system 105 and the external system 125. In an example, the cardiac monitor circuit 160 may be configured to detect a cardiac event, such as a cardiac arrhythmia, or an event leading to worsening heart failure (WHF). The cardiac monitor circuit 160 may process physiologic data acquired by the ambulatory system 105 or received from a data storage device, for patient monitoring, risk stratification, and detection of events indicating presence, onset, termination, improvement, or worsening of a cardiac disease. In certain examples, the cardiac monitor circuit 160 may include sub-circuits coupled to a physiologic sensor to sense a heart sound signal, and detect one or more heart sound components such as S1, S2, S3, or S4 from the heart sound signal. In some examples, the cardiac monitor circuit 160 may be coupled to an implantable sensor configured to sense an epicardial or endocardial acceleration (EA) signal from a portion of a heart. The EA signal may be indicative of force generated while the heart contracts or relaxes. The EA signal may be correlated to one or more heart sound components, such as the S1, S2, S3 or S4 heart sounds, and may be used to assess cardiac systolic or diastolic function. The cardiac monitor circuit 160 may generate a heart sound metric using the heart sound components. Examples of the cardiac monitor circuit 160 are discussed below, such as with reference to FIG. 6.

The patient management system 100 may include a headgear 170 wearable on a head portion of the patient 102. The headgear 170 may include a wearable or subcutaneously implanted sensor configured to sense heart sound information from the head location. In an example, the headgear sensor may sense a physiologic signal representing cardiac mechanical or acoustic activities originated from the heart. The physiologic signal may include sound wave, vibration, motion, displacement, or acceleration associated with cardiac systole and diastole, heart valve closure and opening, or blood flow through the arteries. One or more of these cardiovascular activities may be conducted through body tissue such as vascular structures, or various soft, cartilaginous, or bony tissue on the skull. The physiologic signal sensed from the headgear sensor may be indicative of or correlated with heart sounds.

The headgear 170 may include a communication circuit to establish data communication with the AMD 110. The headgear 170 may receive commands from the AMD 110 to sense heart sound information from a head location, and transmit the sensed heart sound information to the AMD 110. The cardiac monitor circuit 160 may process the physiologic signal acquired by the headgear sensor to generate a heart sound metric. Additionally or alternatively, the headgear 170 may transmit the heart sound information to the external system 125 for processing, storage, or generating diagnostics such as a detection of WHF event. In an example, the headgear 170 is a leadless device and may communicate with the cardiac monitor circuit 160 or the external system 125 via a wireless link.

The AMD 110 may additionally include a therapy circuit configured to initiate or adjust therapies for treating the cardiac conditions such as cardiac arrhythmias or WHF. The therapy may be delivered to the patient 102 via the lead system 108 and the associated electrodes. The therapies may include electrical, magnetic, or other types of energy. Examples of the therapies may include cardiac pacing, cardioversion, defibrillation, neuromodulation, among other electrostimulation therapies. In an example, the therapy circuit may deliver cardiac resynchronization therapy (CRT) or multi-site pacing of at least one ventricle to rectify dyssynchrony and to improve cardiac function in a CHF patient. The therapy may be initiated, or one or more therapy parameters may be adjusted, based at least on the heart sound metric. In some examples, the AMD 110 may deliver drug therapies or biological therapies, such as via a drug infusion pump or other drug delivery systems.

The external system 125 may include a dedicated hardware/software system such as a programmer, a remote server-based patient management system, or alternatively a system defined predominantly by software running on a standard personal computer. Via a communication link 115, the external system 125 may program the AMD 110 to perform one or more of acquiring physiologic data, performing at least one self-diagnostic test (such as for a device operational status), analyzing the physiologic data to detect a cardiac event such as WHF, or optionally delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of WHF events, responses to therapies delivered to the patient 102, or device operational status of the AMD 110 (e.g., battery status and lead impedance). In some examples, the external system 125 may be configured to control the headgear 170 to sense a physiologic signal that contains heart sound information. The telemetry link 115 may be an inductive telemetry link, a capacitive telemetry link, an acoustic telemetry link, or a radio-frequency (RF) telemetry link, or wireless telemetry based on, for example, "strong" Bluetooth or IEEE 802.11 wireless fidelity "WiFi" interfacing standards, among other configurations and combinations of data source interfacing.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device. The remote device 124 may evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. In some examples, the alert conditions may alternatively or additionally be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning, such as respectively described in commonly-assigned U.S. patent application, entitled, "System and Method for Managing Coordination of Assembled Patient Data in an Automated Patient Management System," Ser. No. 11/121,593, filed May 3, 2005, and U.S. patent application, entitled, "System and Method for Managing Patient Triage in an Automated Patient Management System," Ser. No. 11/121, 594, filed May 3, 2005, the disclosures of which are incorporated by reference. In addition to generating alert notifications, the remote device 124, including the server and the interconnected clients, may also execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a system user such as the patient or a clinician, or to a process including, for example, an instance of a computer program executable in a microprocessor. In an example, the process may include an automated generation of recommendations for therapy; adjustment of one or more therapy control parameters such as electrostimulation timing or sequence, electrostimulation mode or amount of stimulation energy, electrode configurations, or stimulation site selection; or a recommendation for further diagnostic test. In an example, the external device 120 or the remote device 124 may include a respective display unit for displaying the physiologic or functional signals, or alerts, alarms, emergency calls, or other forms of warnings to signal. In some examples, the external system 125 may include an external data processor configured to analyze the physiologic or functional signals received by the AMD 110, and to confirm or reject the detection of the cardiac events such as WHF. Computationally intensive algorithms, such as machine-learning algorithms, may be implemented in the external data processor to process the data retrospectively to detect the cardiac events.

Portions of the AMD 110 or the external system 125 may be implemented using hardware, software, or any combination of hardware and software. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
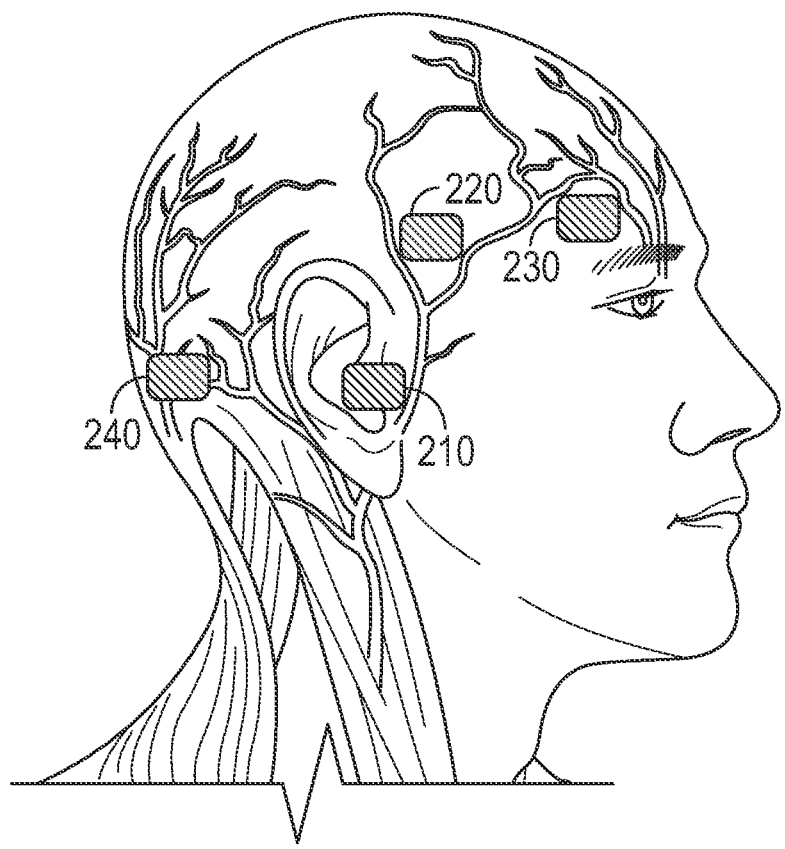
FIG. 2 illustrates, by way of example and not limitation, various locations on the head for positioning a physiologic sensor to sense heart sound information.

FIG. 2 illustrates, by way of example and not limitation, various head locations for placement of a physiologic sensor to sense heart sound information. One or more of such physiologic sensors may be included in or associated with the headgear 170, and are referred to as headgear sensors. The one or more headgear sensors may be non-invasively affixed to areas in proximity to major arteries on the head including, for example, superficial temporal artery, maxillary artery, auricular artery, supraorbital artery, supratrochlear artery, or occipital artery, among others. As discussed above, the headgear sensors may sense physiologic signals representing mechanical or acoustic activities originated from the heart and conducted through various body tissue such as arteries. Physiologic sensors positioned over or near the major arteries on the head may sense mechanical vibration, motion, displacement, or acceleration produced by heart contraction, valvular activities, and pulsatile blood flow through the arteries.

By way of non-limiting example, FIG. 2 illustrates one or more of an auricular sensor 210, a temporal sensor 220, a brow sensor 230, or an occipital sensor 240. The auricular sensor 210 may be placed at an ear canal, a pinna, or behind the ear. The auricular sensor 210 may be in close proximity to the superficial temporal artery or the auricular artery. The superficial temporal artery starts at the termination of the external carotid artery and ascends in front of the ear to the temporal region, and supplies blood to the facial muscles and skin the in frontal and temporal areas. The auricular artery branches from the external carotid artery and runs to the areas around the mastoid process and the ear, providing blood to the ear and the scalp behind the ear. The auricular sensor 210 may sense cardiac vibration or motion conducted through body tissue, including pulsatile arterial waves propagating through the superficial temporal artery or the auricular artery. The signal sensed by the sensor 210 is indicative of or correlated with heart sounds. The temporal sensor 220 may be placed at or near a temple region. The superficial temporal artery and the branches thereof (e.g., parietal and frontal branches) pass through the temporal region. The temporal sensor 220 may sense cardiac vibration or motion conducted through body tissue, including pulsatile arterial waves propagating through the superficial temporal artery or a branch thereof. The brow sensor 230 may be placed at or near the forehead or brow region where the supraorbital artery or the supratrochlear artery passes through. The supraorbital artery and the supratrochlear artery both branch from the ophthalmic artery. The supraorbital artery runs upwards to supply blood to the muscles and skin of the forehead and scalp. The supratrochlear artery passes from the supratrochlear notch to supply blood to the muscles and skin of the scalp. The brow sensor 230 may sense cardiac vibration or motion conducted through body tissue, including pulsatile arterial waves propagating through the supraorbital artery or the supratrochlear artery. The occipital sensor 240 may be placed at or near occipital area through which the occipital artery passes. The occipital artery branches from the external carotid artery and passes to the occipital region, and provides blood flow to the scalp of the back of the head. The occipital sensor 240 may sense cardiac vibration or motion conducted through body tissue, including pulsatile arterial waves propagating through the occipital artery.

Although only one sensor is shown in FIG. 2 at an identified location on the head, this is meant only by way of illustration and not limitation. In some examples, two or more sensors may be placed at an identified location. Alternatively, two or more sensors may be placed at corresponding locations on opposite sides of the head. In an example, two auricular sensors 210 may be respectively plugged into the left and right ear canals. In another example, two temporal sensors 220 may be respectively affixed to the left and right temple regions.

The headgear 170 may hold two or more physiologic sensors, such as the auricular sensor 210, the temporal sensor 220, the brow sensor 230, or the occipital sensor 240. Alternatively, two or more headgears may each accommodate respective physiologic sensors for placement at different head locations. When multiple headgear sensors are used (either placed at or near the same type of arteries at opposite sides of the head, or positioned at or near different types of arteries), each headgear sensor may sense respective physiologic signal containing heart sounds information. The sensed physiologic signals may operatively be transmitted to a central processor within the AMD 110 or the external system 125, where a heart sound metric may be generated. Examples including headgears and the associated sensors to sense heart sound information from various head locations are discussed below, such as with reference to FIGS. 3-4.

Figure 3:
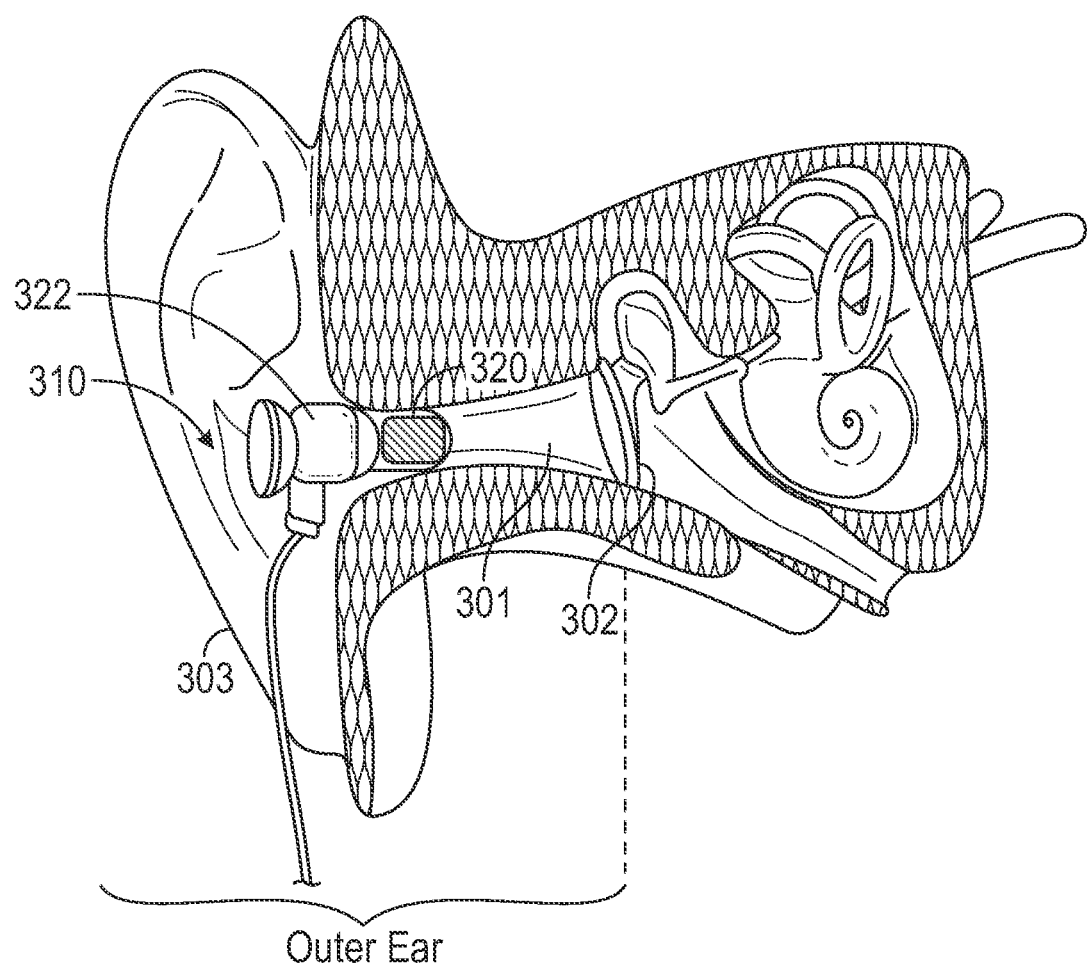
FIG. 3 illustrates an earpiece device configured to be positioned at an outer ear portion of the subject to sense heart sound information therefrom.

FIG. 3 illustrates an earpiece device 310 configured to be positioned at an outer ear portion of the subject to sense heart sound information therefrom. The outer ear is the external portion of the ear, and consists of an auricle 303 and an auditory canal 301 (also known as ear canal). The outer ear gathers sound energy and focuses it on the eardrum 302. The earpiece device 310 represents an embodiment of the headpiece 170 illustrated in FIG. 1, and includes an auricular sensor 320 configured to sense heart sound information from the outer ear portion of the subject.

The earpiece device 310 may be removably inserted within the auditory canal 301. In an example, the earpiece device 310 may be sized and shaped such that it can be frictionally secured inside the auditory canal 301. The earpiece device 310 may include a housing 322 at least partially equipped with one or more of silicone rubber, polymer, or other composite materials to provide frictious interface with the auditory canal 301. Additionally or alternatively, at least a portion of the housing of the earpiece device 310 may be mechanically textured to have a rough and corrugated surface finish to increase the friction and prevent the earpiece device 310 from slipping in the auditory canal 301. In some examples, the earpiece device 310 may include an anchoring element configured to attach to an anatomical structure, such as one or both ears, the nose, the scalp, or the neck. Examples of the anchoring element may include a hook, a ring, a band, or a clip, among others. In an example, the earpiece device 310 has a shape analogous to an earphone or earbuds for plugging into the ear canal 301.

The earpiece device 310 may alternatively be positioned at other locations of the outer ear. In an example, the earpiece device 310 may be removably affixed to a portion of an auricle (also known as pinna), such as via one or more affixation elements such as a clip, a hook, glue, or other non-invasive affixation means. Alternatively, the earpiece device 310 may be invasively attached to the auricle through a pierced hole on the ear lobe or other portions of the auricle, such as in a similar fashion to an earring or an ear-stud. In another example, the earpiece device 310 may be included as a part of an ear cover or earmuff configured to interface tightly with one or both auricles such as via compression. In another example, the earpiece device 310 may be attached to the back of the ear (e.g., behind the pinna), such as in a similar fashion to a behind-the-ear hearing aid.

In various examples, the earpiece device 310 or a variant thereof may be implanted subcutaneously and affixed to an anatomical structure, such as the temporal bone or the surrounding subcutaneous tissue. The earpiece device 310 may have gripping elements to bond the earpiece device 310 to a body part of the patient. Examples of the gripping elements may include penetrators such as spikes, pins, or barbs protruding from the exterior surface.

The auricular sensor 320, which represents an embodiment of the auricular sensor 210, is configured to sense heart sound information from the ear canal 301. In an example, the auricular sensor 320 may be an accelerometer sensor, such as a piezoelectric crystal (e.g., quartz) accelerometer or capacitive accelerometer, fabricated using micro electromechanical systems (MEMS) technology.

Alternatively, the auricular sensor 320 may include an acoustic sensor, a microphone, or other vibrational or acoustic sensors. The auricular sensor 320 may sense mechanical vibration, motion, displacement, or acceleration produced by cardiac and valvular activities and conducted through body tissue including, for example, arteries such as auricular artery, superficial temporal artery, or the branches therefrom, and/or other soft, cartilaginous, or bony tissue on the skull. The auricular sensor 320 may also sense vibration and motion of the eardrum 302 in response to the conducted cardiac, valvular, and arterial activities.

In some examples, the headgear 170 comprises two earpieces 310 configured for insertion and remaining in the ear canals, or attached to an outer ear portions, of both the left and right ears. The auricular sensors 320 associated with the two earpieces 310 may sense respective physiologic signals indicative of or correlated with heart sounds. A composite heart sound signal may be generated using multiple headgear sensor signals (such as those sensed by two earpieces from both ears), and a heart sound metric may be generated for medical diagnostics and therapy decisions, as to be discussed further in FIG. 5.

Figure 4:
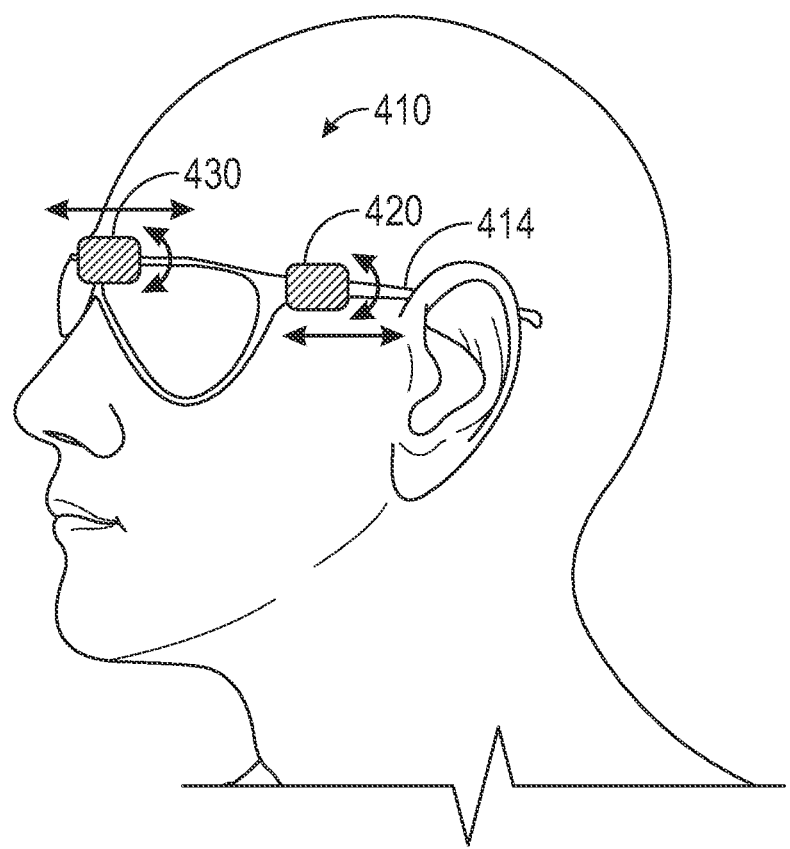
FIG. 4 illustrates an eyewear configured to sense heart sound information from one or more head locations near the subject's eyes.

FIG. 4 illustrates an eyewear 410 configured to sense heart sound information from one or more head locations near the subject's eyes. The eyewear 410 represents an embodiment of the headpiece 170 illustrated in FIG. 1, and may have a shape analogous to eyeglasses or goggles. The eyewear 410 includes an eyepiece 412 to be positioned close to one or both eyes, and two side elements 414 extending over the ears or the back of the head, analogous to the long arms on the left and right sides of the eyepieces.

The eyewear 410 may include one or more of a temple-piece 420 or a brow-piece 430. The temple-piece 420 may include a sensor that represents an embodiment of the temporal sensor 220, and may be sized and shaped to be in contact with a temple region of the subject. The temple-piece 420 may be adjustably attached to one of the side elements 414. In an example, the temple-piece 420 may translate along the length of a side element 414, or rotate around the axis of the side element 414 to improve flexible temple contact. The brow-piece 430 may include a sensor that represents an embodiment of the brow sensor 230, and may be sized and shaped to interface with the supraorbital region of the subject's forehead. The brow-piece 430 may be adjustably attached to the eyepiece 412, or the connective bridge between the rims of the eyepiece 412. Similar to the temple-piece 420, the brow-piece 430 may move with multiple degrees of freedom, such as longitudinal translation and rotational movement with respect to the connective bridge or the eyepiece 412.

The temple-piece 420 and the brow-piece 430 are each configured to sense, from respective head locations, physiologic signals that contain heart sound information. In an example, the temple-piece 420 and the brow-piece 430 may each include an accelerometer configured to detect mechanical vibration, motion, displacement, or acceleration produced by heart contraction and valvular activities and conducted through body tissue including, for example, soft, cartilaginous, or bony tissue on the skull. In an example, the temple-piece 420 may sense arterial waves propagating through the superficial temporal artery and the branches therefrom. The brow-piece 430 may sense arterial waves propagating through the supraorbital artery or the supratrochlear artery.

In some examples, the eyewear 410 may comprise two or more temporal sensors 420 such as adjustably attached to the left and right arms 414. The eyewear 410 may additionally or alternatively comprise two or more brow sensors 430. A composite heart sound signal may be generated using the physiologic signals acquired by the temporal sensors 420 and/or the brow-piece 430. A heart sound metric may be generated using the composite heart sound signal, and used in applications of medical diagnostics (e.g., worsening heart failure) and therapy delivery.

Figure 5:
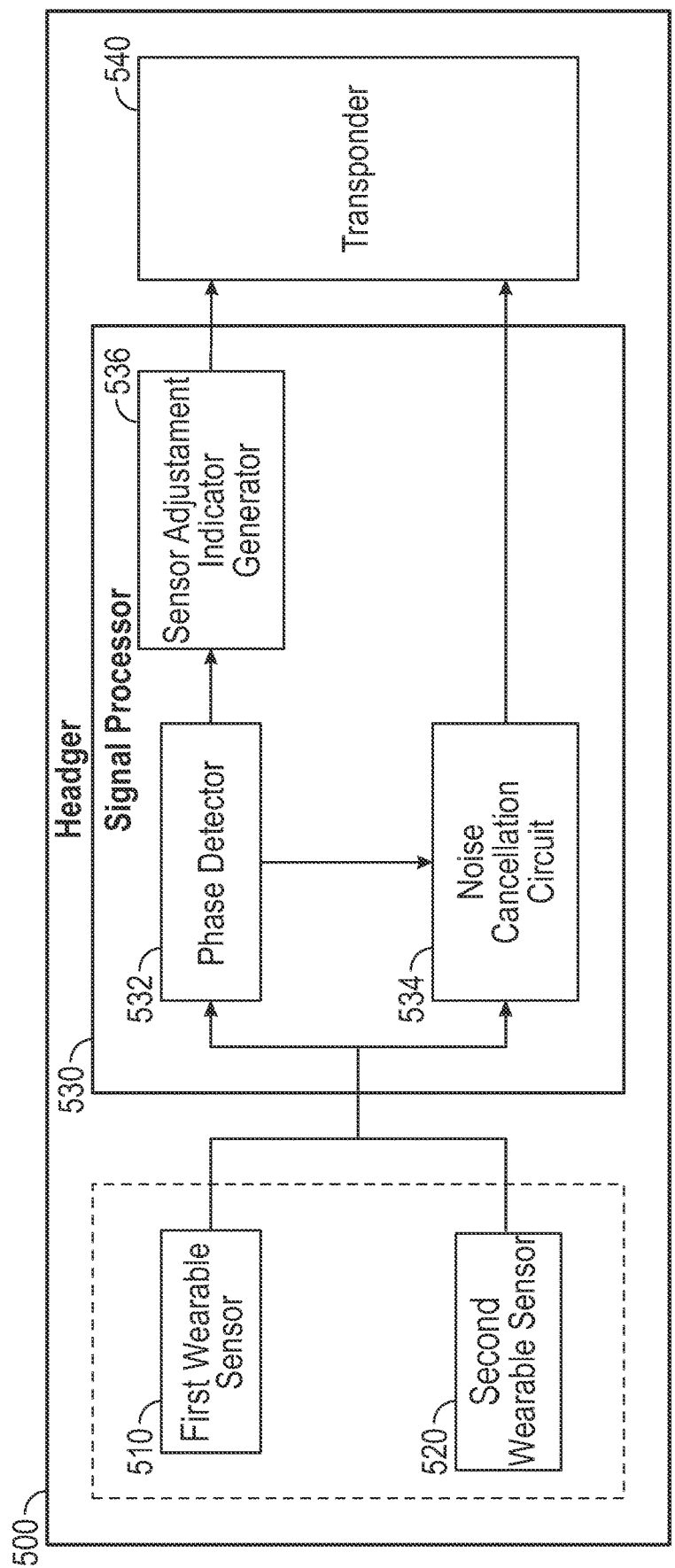
FIG. 5 is a diagram illustrating an example of a headgear configured to be worn by subject and to collect heart sound information.

FIG. 5 illustrates a block diagram illustrating an example of a headgear 500 wearable on a subject and configured to collect heart sound information. The headgear 500 may be implemented in the earpiece device 310 illustrated in FIG. 3 or the eyewear 410 illustrated in FIG. 4. Alternatively, the headgear 500 may have other shapes, designs, or structures, and may be implemented in a headband, braces, a helmet, or a hood, among others.

The headgear 500 comprises at least a first wearable sensor 510 and a second wearable sensor 520, a signal processor 530, and a transponder 540. Some or all of these components may be enclosed within a housing. The headgear 500 may additionally include an interface to maintain physical contact with a head site, such as an outer ear, a temple, or the forehead, among other locations. In some examples, the headgear 500 may include a power source. The power source may include a rechargeable battery, a supercapacitor, or other power supplies. The rechargeable power source may be charged wirelessly by a portable device such as a handheld device with circuitry configured to transfer energy to the rechargeable power source through electromagnetic induction.

The first and second wearable sensors 510 and 520 may sense respectively first and second physiologic signals at various head locations, denoted by X1(t) and X2(t), where "t" represents the time. The sensed physiologic signals may represent sound waves, vibration, motion, displacement, or acceleration associated with cardiac systole and diastole, heart valve closure and opening, or blood flow through the arteries. One or more of these cardiovascular activities may be conducted through body tissue such as vascular structures, and various soft, cartilaginous, or bony tissue on the skull. Examples of the wearable sensors 510 or 520 may include the auricular sensor 210, the temporal sensor 220, the brow sensor 230, the occipital sensor 240, as discussed above with reference to FIGS. 2-4. It is to be noted that the two wearable sensors 510 and 520 are just for illustration but not limitation. It will be appreciated by those skilled in the art that additional physiologic sensors may be associated with the headgear 500, and collect heart sound information from various head locations.

The first and second wearable sensors 510 and 520 may be placed at opposite head locations. In various examples, the first and second wearable sensors 510 and 520 may be positioned over or near one or more of major arteries on the head, as discussed above in reference to FIG. 2. In an example, the sensors 510 and 520 may be included in respective earpieces analogous to the earpiece device 310. The earpieces are configured for placement in the left and right ear canals or other outer ear portions, and sense motion and vibrations indicative of heart sounds. In another example, the sensors 510 and 520 are temporal sensors, each analogous to the temple-piece 420. The sensors 510 and 520 are configured to be adjustably positioned at the left and right temples to sense arterial waves and vibrations conducted through body tissue such as the skull.

The signal processor 530 may generate a composite signal using the first signal X1(t) and the second signal X2(t) respectively sensed by the first and second sensors 510 and 520, and generate a heart sound metric using the composite signal. The signal processor 530 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The signal processor 530 may include circuit sets comprising one or more other circuits or sub-circuits, such as a phase detector 532, a noise cancellation circuit 534, and a sensor adjustment indicator generator 536. These circuits may, individually or collectively, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The phase detector 532 may pre-process the sensed physiologic signals X1(t) and X2(t), including amplification, digitization, filtering, or other signal conditioning operations. The phase detector 532 may time-synchronize the physiologic signals X1(t) and X2(t) to remove or substantially reduce the data acquisition system delay or physiologic delay between the X1(t) and X2(t) sensed at different head locations (e.g., left ear canal vs. right ear canal). The phase detector 532 may then detect a phase relationship between the signals X1(t) and X2(t). In an example, the sensed physiologic signal X1(t) includes a signal of interest S1(t) and a motion interference N1(t), that is, X1(t)=S1(t)+N1(t). The signal of interest S1(t) represents cardiac, valvular, and arterial activities, and contains heart sound information. The motion interference N1(t) represents artifacts associated with patient locomotion or physical activity. Similarly, the sensed physiologic signal X2(t) includes a signal of interest S2(t) and a motion interference N2(t), that is, X2(t)=S2(t)+N2(t). S2(t) represents cardiac, valvular, and arterial activities and indicative of heart sounds, and N2(t) represents artifacts associated with patient locomotion or patient physical activity. In an example, the phase detector 532 may detect the motion interference components N1(t) and N2(t), and detect a phase relationship between N2(t) and N2(t).

The noise cancellation circuit 534 may generate a composite signal (denoted by Y(t)) using the sensed physiologic signals X1(t) and X2(t) and the phase relationship as determined by the phase detector 532. In an example, the composite signal may be computed using a linear or a nonlinear combination of the signals X1(t) and X2(t). In another example, the combination of signals may be performed in a frequency domain or other transformed domain. In an example, one of the signals X1(t) or X2(t) may be phase-shifted in accordance with the determined phase relationship between N1(t) and N2(t), and combined with the other of the signals X1(t) or X2(t) to generate the composite signal Y(t). In an example, corresponding to two headgear sensors that are placed on opposite head locations (such as left and right ears, or left and right temples), the phase detector 532 may detect a phase shift between N1(t) and N2(t) of substantially 180 degrees (e.g., within a specified margin of approximately 10 degrees around 180 degrees), indicating that the interferences N1(t) and N2(t) are substantially out of phase. The noise cancellation circuit 534 may generate the composite signal Y(t) by adding the second signal X2 (t) and the first signal X1(t) to substantially remove or attenuate the motion interference from the first physiologic signal. The resulting composite signal Y(t) may have a higher signal to noise/interference ratio.

Detecting the phase relationship between the physiologic signals X1(t) and X2(t) acquired from two wearable sensors as discussed herein may improve the heart sound sensing in noisy environment, such as when the subject is engaging in physical activities. For example, because the detected phase shift may indicate an ongoing locomotion or other physical activities, no dedicated hardware and resources are required to sense and process the physical activity. The detected phase shift may be used to produce a clean composite signal Y(t) free of, or less affected by, motion artifacts. As such, the heart sound components may be more reliably detected, the cardiac systolic and diastolic functions may be more accurately characterized, and the medical diagnostic (e.g., worsening of heart failure) accuracy and timeliness may be improved.

In various examples, the noise cancellation circuit 534 may include a filter circuit or a filter bank configured to filter one or both of the physiologic signals X1(t) and X2(t) to substantially remove or attenuate respective motion interferences. The filter circuit may include an adaptive filter configured to adaptively filter the first sensed signal X1(t) using the interference component N2(t) contained in the second sensed signal X2(t). The interference N2(t), such as motion artifacts associated with locomotion or physical activity, is correlated with the interference N1(t), but uncorrelated with the signal component S1(t), of the first signal X1(t). The adaptive filter is capable of adjusting the filter weights, and thus its impulse response, to minimize an error signal, which is dependent on the filter output. The adjustment of the filter weights is governed by an adaptive algorithm. With adaptive control, noise reduction can be accomplished with little risk of distorting the signal. The error signal to be used depends on the application. The criteria to be used may be the minimization of the mean-squared error, the temporal average of the least-squared error etc. Different algorithms may be used for each of the minimization criteria, such as the Least Mean Squares (LMS) algorithm, the Recursive Least Squares (RLS) algorithm, among others. When the error signal satisfies a specific condition (such as below an error bound), the adaptation process may stop, and the noise cancellation circuit 534 may generate the composite signal Y(t) using the adaptively filtered first physiologic signal X1(t).

The phase relationship such as between the motion interference N1(t) of the first sensed signal X1(t) and the motion interference N2(t) of the second sensed signal X2(t) may be used to trigger the sensor adjustment indicator generator 536 to generate a notification to the subject. For example, if the phase shift between N1 (t) and N2(t) is not substantially 180 degrees (e.g., falls outside a range such as 180 degrees plus or minus a margin), then a notification may be generated and alert the subject to adjust the position of one or more physiologic sensors. For example, a user, such as the patient, may re-position the earpiece device 310 in the left or right ear canal, or sliding or rotating the temple-piece 420 on the left or right arm of the eyewear 410. The phase shift between N1(t) and N2(t) may be monitored during the sensor position adjustment, and the adjustment may be repeated until the phase shift between N1(t) and N2(t) is substantially out of phase.

The transponder 540 may establish a communication with another device or system, such as the AMD 110 or the external system 125. In an example, and transmit the sensory information including the composite signal and the sensor adjustment indicator to the AMD 110 or the external system 125, and/or receive programming instructions from the AMD 110 or the external system 125. The communication can be through a wired communication connection such as a cable coupled to a communication interface on the communicator, or a wireless connection such as the Bluetooth protocol, IEEE 802.11 wireless, an inductive telemetry link, or a radio-frequency telemetry link, among others. In an example, the headgear 500 may communicate with the AMD 110 via an intermediate device, such as a portable device. The portable device may be communicatively coupled the headgear 500 via a Universal Serial Bus (USB) connection or a Bluetooth connection. The portable device may further be in communication with the AMD 110. In an example, the portable device is a handheld device that allows a user, such as the patient, to control data communication between the headgear 500 and the portable device.

Figure 6:
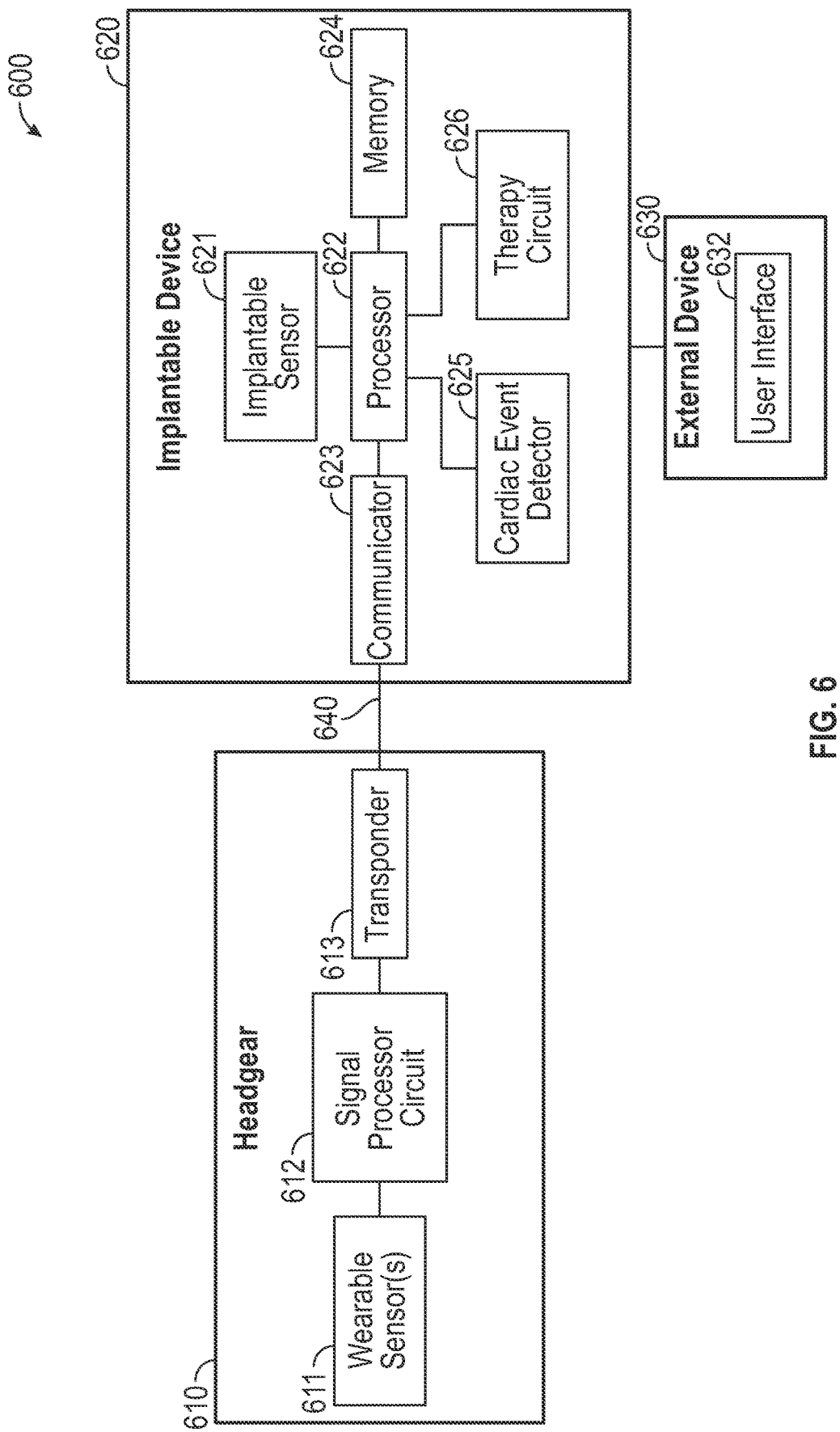
FIG. 6 is a diagram illustrating an example of a cardiac function monitoring system that includes a headgear configured to sense heart sound information from a subject.

FIG. 6 is a diagram illustrating an example of a cardiac function monitoring system 600 that includes a headgear configured to sense heart sound information from a subject. The cardiac monitoring system 600 may monitor cardiac function, such as a progression of a heart failure or other cardiac disease, and generate diagnostic decisions, recommend treatment, or deliver therapies to restore or improve cardiac condition. The cardiac monitoring system 600 may be implemented between the AMD 110 and the headgear 170, or among the AMD 110, the headgear 170, and the external system 125.

The cardiac monitoring system 600 may include one or more of a headgear 610, an implantable device 620, and an external device 630. The headgear 610 may be sized and shaped to be worn on a patient's head, and represents an embodiment of the headgear 500 and implemented as the earpiece device 310 or the eyewear 410, among other designs, shapes, or configurations. The headgear 610 may include a wearable sensor 611, such as one of the auricular sensor 210, the temporal sensor 220, the brow sensor 230, the occipital sensor 240, among others. The wearable sensor 611 is configured to sense a physiologic signal $X_H(t)$ representing vibration, motion, displacement, or acceleration associated with cardiac, valvular, and arterial activities. The signal $X_H(t)$ contains heart sound information. The signal processor circuit 612 may amplify, digitize, and filter the sensed physiologic signal. In an example, the signal processor circuit 612 may determine a phase relationship between two wearable sensors associated with the headgear 610, as discussed above with reference to FIG. 5.

The transponder 613, which represents an embodiment of the transponder 540, may transmit at a portion of the physiologic signal indicative of heart sounds to the implantable device 620 via a communication link 640. In an example, the communication link 640 is a wireless communication link, such as a radiofrequency, inductive, capacitive, optical, or acoustic communication, or any other means suitable for communication. In some examples, the transponder 613 may communicate information, such as sensed signals, data, messages, or instructions, with the external system 125 or another external system separated from the external system 125 via the communication link 640.

The implantable device 620, which represents an embodiment of the AMD 110 in FIG. 1, may include a communication circuit 623, a processor circuit 622, a memory 624, an implantable sensor 621, and a cardiac event detector 625. In some examples, the implantable device 620 may additionally include a therapy circuit 626. Through the communication circuit 623, the implantable device 620 may receive the signals, data, or messages from the headgear 610, such as a physiologic signal $X_H(t)$ indicative of heart sounds. The implantable sensor 621 may sense a physiologic signal $X_I(t)$ from the subject, such as when the heart undergoes an intrinsic rhythm or when the heart undergoes electrostimulation. In an example, the physiologic signal $X_I(t)$ is a cardiac electrical signal, such as electrocardiograms (ECGs) such as sensed by using electrodes non-invasively attached to the body surface, subcutaneous ECGs such as sensed by using subcutaneously placed electrodes, or intracardiac electrograms (EGMs) such as sensed by using electrodes on one or more leads such as the lead system 108 or the can housing of the AMD 110. In another example, the signal $X_I(t)$ is a cardiac mechanical signal, such as a heart sound signal or cardiac or a thoracic impedance signal. In yet another example, the signal $X_I(t)$ is a respiration signal or one or more respiratory parameters such as a tidal volume, a respiration rate, a minute ventilation, a respiratory sound, or a rapid-shallow breathing index (RSBI) computed as a ratio of a respiratory rate measurement to a tidal volume measurement. In another example, the signal $X_I(t)$ is a hemodynamic signal, such as arterial pressure, pulmonary artery pressure, left atrial pressure, RV pressure, LV coronary pressure; thoracic impedance or cardiac impedance; blood temperature; blood oxygen saturation; central venous pH value or oxygen or carbon dioxide level in the blood or other tissue or organs in the body, among others.

In an example, the implantable sensor 621 is configured to sense a heart sound signal $X_I(t)$. Examples of the implantable sensor 621 may include an accelerometer, an acoustic sensor, a microphone, a piezo-based sensor, or other vibrational or acoustic sensors. The implantable sensor 621 may be enclose in a housing of the implantable device such as the AMD 110, or associated with a lead such as the lead system 108 operatively in connection with the AMD 110. In some examples, the implantable sensor 621 may be an implantable accelerometer configured to sense an epicardial or endocardial acceleration (EA) signal $X_I(t)$ from a portion of a heart, such as on an endocardial or epicardial surface of one of a left ventricle, a right ventricle, a left atrium, or a right atrium. The EA signal may contain components corresponding to first (S1), second (S2), third (S3), or fourth (S4) heart sound. In this document, the EA signal is also referred to as the "heart sound signal." EA components that correspond to S1, S2, S3 or S4 heart sounds are also reference to as respective heart sound components.

The processor 622 represents an embodiment of the cardiac monitor circuit 160 illustrated in FIG. 1. The processor 622 may be coupled to the implantable sensor 521 to process the sensed heart sound signal $X_I(t)$, including amplifying, digitizing, filtering, among other processing. In an example, the received heart sound signal may be band-filtered filtered to a frequency range of approximately between 5 and 90 Hz, or approximately between 9 and 90 Hz. In an example, the processor 622 may include a double or higher-order differentiator configured to calculate a double or higher-order differentiation of the heart sound signal. The processor 622 may compute an ensemble average of the heart sound signal $X_I(t)$ over multiple cardiac cycles, or over a specified time period such as one minute, ten minutes, one hour, one day, etc. The processor 622 may generate respective time windows for detecting one or more heart sound components from an ensemble averaged heart sound signal. The time windows may be determined with reference to a physiologic event such as Q wave, R wave, or QRS complexes detected from a surface ECG, a subcutaneous ECG, or cardiac sensing events in an intracardiac EGM.

As illustrated in FIG. 2, the processor 622 may be coupled to the communicator circuit 623 to receive the physiologic signal $X_H(t)$ indicative of heart sound received from the headgear 610. In an example, the processor 622 may generate a composite heart sound signal Y(t) using the physiologic signal $X_H(t)$ received from the headgear 610 and the heart sound signal $X_I(t)$ sensed by the implantable sensor 621. The composite signal may be a linear or nonlinear combination of $X_H(t)$ and $X_I(t)$. The processor 622 may detect one or more heart sound components, or to generate a heart sound metric using the composite signal Y(t).

In another example, the implantable sensor 621 may sense a cardiac electrical signal $X_I(t)$ such as a ECG or EGM signal. The processor 622 may detect from $X_I(t)$ timing of the Q wave, R wave, QRS complex, or localized cardiac depolarization, and determine time windows for detecting one or more heart sound components (e.g., S1 window, S2 window, S3 window, or S4 window) based on the timing information of cardiac activation. The processor 622 detect from the headgear signal $X_H(t)$ one or more heart sound components, or generate a heart sound metric, using the timing information of cardiac activation or the time windows. By way of non-limiting example, an S1 detection window may begin at 50 milliseconds (msec) following an R wave (or a localized ventricular depolarization) and have a duration of 300 msec. An S2 detection window may begin at specified offset following a detected R wave (or a localized ventricular depolarization) or S1 heart sound. An S3 detection window may be determined using at least one cardiac signal feature such as the R-wave timing or the timing of S2 heart sound. The S3 detection window may have a specified duration and may begin at a specified offset following the detected S2. In an example, the offset may be 125 msec, and the S3 window duration may be 125 msec. The offset or the S3 window duration may be a function of a physiological variable such as a heart rate. For example, the offset may be inversely proportional to the heart rate, such that the S3 detection window may start at a smaller offset following the S2 at a higher heart rate.

The processor 622 may detect one or more heart sound components from $X_H(t)$ within the respective heart sound detection window. The detection of heart sound components may be based on an amplitude or signal energy within the respective heart sound window. In an example, the processor 622 may detect a heart sound component adaptively by tracking the temporal locations of the previously detected heat sound features. For example, an S3 heart sound may be detected by adaptively tracking the timing of historically detected S3 heart sounds. A dynamic programming algorithm may be used to detect and track the S3 heart sound within the S3 detection window, such as that disclosed in the commonly assigned Patangay et al. U.S. Pat. No. 7,853,327 entitled "HEART SOUND TRACKING SYSTEM AND METHOD," which is hereby incorporated by reference in its entirety.

The processor 622 may generate one or more heart sound metric using the detected heart sound components. The heart sound metric may include temporal, statistical, or morphological features of one or more detected heart sound components. Examples of the heart sound metric may include an intensity, such as an amplitude, a spectral density, a root-mean-squared value, or signal energy of a detected heart sound component within a hear sound detection window. Alternatively or additionally, the heart sound metric may include cardiac timing intervals (CTI) between a cardiac electrical event (such as detected from the cardiac electrical signal $X_I(t)$) and a mechanical event (such as detected from the signal $X_H(t)$). The CTI may include a pre-ejection period (PEP), a systolic timing interval (STI), or a diastolic timing interval (DTI), among others. The PEP represents the total duration of the electrical and mechanical events prior to ejection, and can be measured as the time duration from the onset of the QRS to the S1 heart sound, that is, PEP≈Q–S1 interval. The STI represents the duration of total electro-mechanical systole, and contains two major components, namely the PEP and the LVET. The STI can be measured as an interval from the onset of the QRS complex on the ECG or the atrial activation event in an intracardiac EGM to the S2 heart sound, that is, STI≈Q-S2 interval. The DTI represents the duration of total electro-mechanical diastole. The DTI spans from the closure of the aortic valve to the onset of the atrial depolarization in the next cardiac cycle. In an example, the DTI can be measured as the interval from the S2 heart sound to the onset of the QRS complex on the ECG or the atrial activation event in an intracardiac EGM of the next cardiac cycle, that is, DTI≈S2-Q interval. In some examples, the heart sound metric generator circuit 222 may generate composite measures such as PEP/LVET ratio, STI/DTI ratio, STY cycle length (CL) ratio, or DTI/CL ratio, among others.

The heart sound metrics, among other information such as the signals $X_I(t)$ and $X_H(t)$ and the heart sound components, may be presented to a user to a process. In an example, the heart sound metrics and the aforementioned information may be stored in the memory 624. Additionally or alternatively, the cardiac event detector 625 may use the heart sound metrics and other information to detect a cardiac event. In an example, the cardiac event detector 625 may detect a worsening heart failure (WHF) by comparing a heart sound metric to a detection threshold. In some examples, the cardiac event detector 625 may generate a composite signal index using a combination of various signal metrics including the heart sound metric, and generate a WHF alert when the composite signal index exceeds a detection threshold. In some examples, the cardiac event detector 625 may trend the heart sound metric (e.g., S3 trend) over time, and generate a predictor trend indicating temporal changes of the signal metric trend. The temporal change may be calculated using a difference between short-term values and baseline values. The short-term values may include statistical values such as a central tendency of the measurements of the signal metric within a short-term window of a first plurality of days. The baseline values may include statistical values such as a central tendency of the measurements of the signal metric within a long-term window of a second plurality of days preceding the short-term window in time. In some examples, the predictor trend may be determined using a linear or nonlinear combination of the relative differences between multiple short-term values corresponding to multiple first-time windows and multiple baseline values corresponding to multiple second time windows. The differences may be scaled by respective weight factors that may be based on timing information associated with corresponding multiple short-term window, such as described by Thakur et al., in U.S. Patent Publication 2017/0095160, entitled "PREDICTIONS OF WORSENING HEART FAILURE", which is herein incorporated by reference in its entirety.

The external device 630, which represents an embodiment of the external system 125, may include a user interface 632 configured to receive user programming of the headgear 610 and the implantable device 620 and to output the sensed signals and detection results. In an example, the user interface 632 may include a display screen to display the detected cardiac event (e.g., WHF event), the heart sound metrics, the heart sound components, sensed signals $X_I(t)$ and $X_H(t)$, among other intermediate measurements or calculations. The information may be presented in a table, a chart, a diagram, or any other types of textual, tabular, or graphical presentation formats. The presentation of the output information may include audio or other media format. In an example, alerts, alarms, emergency calls, or other forms of warnings may be generated to signal the system user about the detected cardiac event.

The optional therapy circuit 626 may be configured to deliver a therapy to the patient in response to the detected cardiac event. Examples of the therapy may include electrostimulation therapy delivered to the heart, a nerve tissue, other target tissue, a cardioversion therapy, a defibrillation therapy, or drug therapy including delivering drug to a tissue or organ. In some examples, the therapy circuit 250 may modify an existing therapy, such as adjust a stimulation parameter or drug dosage.

Although the discussion herein focuses on WHF event detection, this is meant only by way of example but not limitation. Systems, devices, and methods discussed in this document may also be suitable for detecting various sorts of diseases or for assessing risk of developing other worsened conditions, such as cardiac arrhythmias, heart failure decompensation, pulmonary edema, pulmonary condition exacerbation, asthma and pneumonia, myocardial infarction, dilated cardiomyopathy, ischemic cardiomyopathy, valvular disease, renal disease, chronic obstructive pulmonary disease, peripheral vascular disease, cerebrovascular disease, hepatic disease, diabetes, anemia, or depression, among others.

FIGS. 7A-7C are graphs illustrating, by way of example and not limitation, physiologic signals recorded by accelerometer sensors included in two earpiece devices such as the earpiece device 310 as illustrated in FIG. 3. One earpiece is plugged into the auditory canal of the left ear, and the other earpiece is plugged into the auditory canal of the right ear of a subject. The physiologic signals were concurrently recorded during brisk walking (prior to the time instant $T_0$) and during rest (after the time instant $T_0$). FIG. 7A illustrates overlay plots of the left-ear accelerometer signal $X_L(t)$ 710 and the right-ear accelerometer signal $X_R(t)$ 720. The recorded signals $X_L(t)$ and $X_R(t)$ each include a signal-of-interest component ($S_L(t)$ and $S_R(t)$, respectively) and noise or inference components, including motion artifacts ($N_L(t)$ and $N_R(t)$, respectively). The signals of interest, $S_L(t)$ and $S_R(t)$, contain heart sound information, and represent motion, vibration, displacement, or acceleration associated with cardiac, valvular, and arterial activities that are conducted through the vascular structure and/or other soft, cartilaginous, or bony tissue on the skull. The motion artifacts $N_L(t)$ and $N_R(t)$ can be profound during walking or other physical activities. Due to their substantially symmetric placement on opposite sides of the skull, the motion artifacts in $X_L(t)$ and $X_R(t)$ are substantially out of phase (i.e., a phase shift of approximately 180 degrees). FIG. 7B illustrates overlay plots of $X_L(t)$ and an inverted $X_R(t)$. The inversion of $X_R(t)$ entails a 180-degree phase shift, making the positive components of $X_R(t)$ negative and the negative components positive. The $X_L(t)$ and the inverted $X_R(t)$ are substantially in phase, suggesting that $X_L(t)$ and $X_R(t)$ are substantially out of phase. Physical activities such as walking do not substantially alter the phase relationship between the signal-of-interest $S_L(t)$ and $S_R(t)$ contained in the respective signals $X_L(t)$ and $X_R(t)$. $N_L(t)$ and $N_R(t)$ may be detected, and their phase relationship during physical activity may be detected, such as via the phase detector 532 illustrated in FIG. 5. A notification may be generated, such as via the sensor adjustment indicator generator 536, to alert the patient to re-position one or both of the earpieces until the motion interferences $N_L(t)$ and $N_R(t)$ are substantially out of phase.

FIG. 7C illustrates a composite signal Y(t) generated using a linear or a nonlinear combination of the signals $X_L(t)$ and $X_R(t)$, such as generated by the noise cancellation circuit 534. In an example where the motion artifacts components of the sensed signals $X_L(t)$ and $X_R(t)$ are out of phase (as illustrated in FIGS. 7A-7B), the composite signal Y(t) 730 may be determined by adding the right-ear accelerometer signal $X_R(t)$ and the left-ear accelerometer signal $X_L(t)$ to substantially remove or attenuate the motion interference $N_L(t)$. From the composite signal Y(t), heart sound components, such as S1 component 731A and S2 component 732A during the physical activity, or S1 component 731B and S2 component 732B during rest, may be detected. The detected heart sound components may be used to generate a heart sound metric, such as by the processor 622 in FIG. 6.

Figure 8:
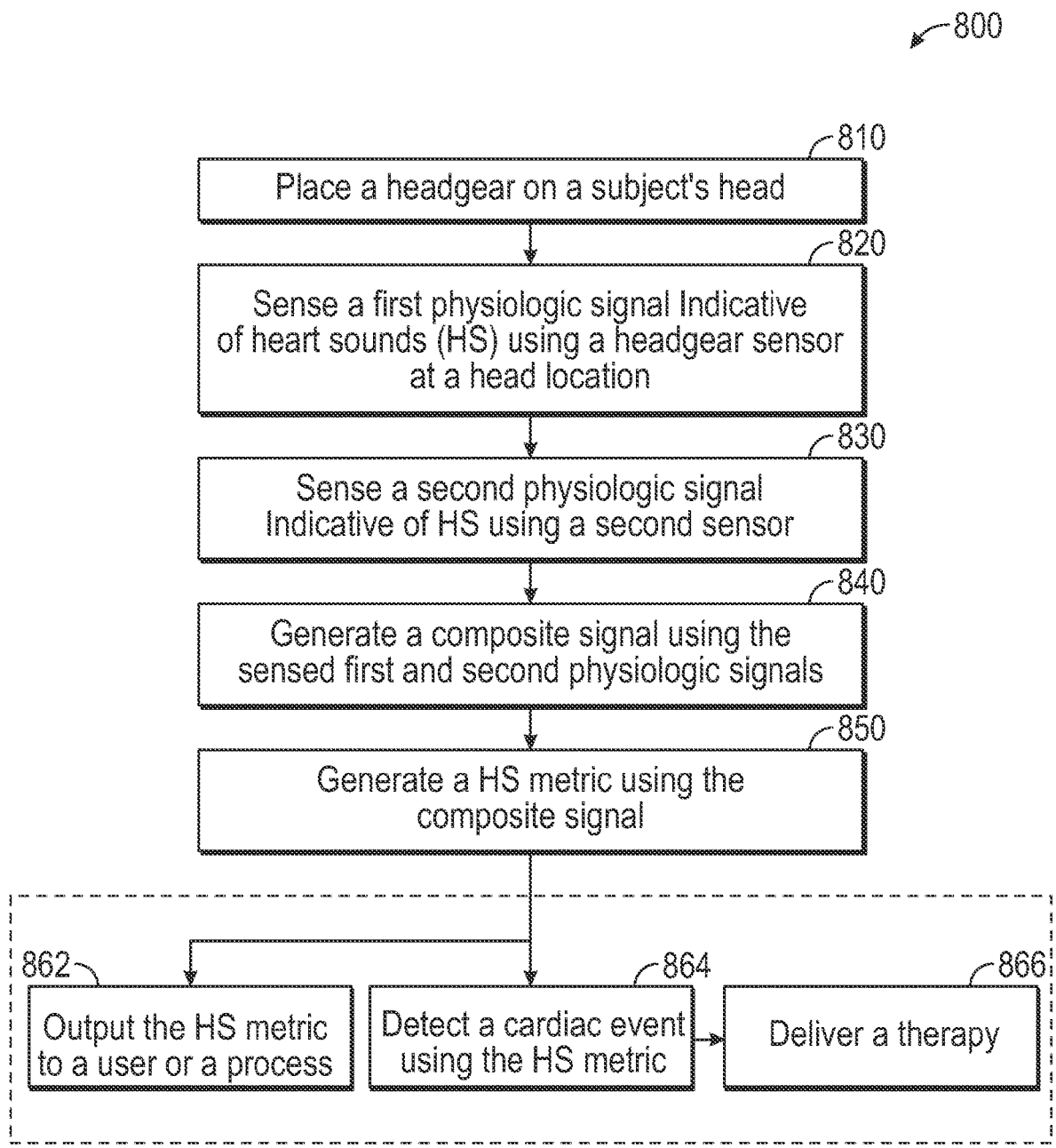
FIG. 8 is a flowchart illustrating an example of a method for sensing heart sound information from a subject using a medical system that includes a headgear wearable on a subject's head.

FIG. 8 is a flowchart illustrating an example of a method 800 for sensing heart sound information from a subject using a medical system that includes a headgear wearable on a subject's head. The method 800 may be used to operate the headgear 170 as illustrated in FIG. 1, the earpiece device 310, the eyewear 410, or any variant thereof.

The method 800 commences at 810, where a headgear may be placed on the head of the subject. As previously discussed, the headgear may include one or more physiologic sensors each configured to be attached to various head locations in proximity to major arteries on the head, such as superficial temporal artery, maxillary artery, auricular artery, supraorbital artery, supratrochlear artery, or occipital artery. The physiologic sensors on the headgear may be configured to sense mechanical vibration, motion, displacement, or acceleration produced by heart contraction, valvular activities, and pulsatile blood flow through the arteries. Examples of the physiologic sensor associated with the headgear may be an accelerometer sensor, such as a piezoelectric crystal (e.g., quartz) accelerometer or capacitive accelerometer, fabricated using micro electro-mechanical systems (MEMS) technology. Alternatively, the physiologic sensor may include an acoustic sensor, a microphone, or other vibrational or acoustic sensors.

Based on the head locations where the headgear sensors are placed to sense the first physiologic signal, the headgear sensors may include the auricular sensor 210, the temporal sensor 220, the brow sensor 230, or the occipital sensor 240, as illustrated in FIG. 2. In various examples, two or more physiologic sensors may be positioned on an identified head location, or positioned at different head locations on the left and right sides of the head. In an example, two auricular sensors may be respectively positioned in the left and right ear canals. In another example, two temporal sensors may be respectively positioned on the left and right temples.

At 820, a first physiologic signal indicative of heart sounds may be sensed using the headgear sensor at a head location. The first physiologic signal may represent mechanical or acoustic activities originated from the heart. The first physiologic signal may include sound wave, vibration, motion, displacement, or acceleration associated with cardiac systole and diastole, heart valve closure and opening, or blood flow through the arteries. One or more of these cardiovascular activities may be conducted through body tissue such as vascular structures, and various soft, cartilaginous, or bony tissue on the skull. The physiologic signal sensed from the headgear sensor may be indicative of or correlated with heart sounds.

At 830, a second physiologic signal indicative of heart sounds may be sensed using a second physiologic sensor. The second physiologic sensor may be placed at a body location different from the head location where the first physiologic signal is sensed. In an example, the second physiologic sensor may be included in the same headgear that includes the first physiologic sensor. Alternatively, the second physiologic sensor may be included in a different headgear. In an example, the first and second physiologic sensors are respectively included in two earpieces for insertion with the ear canals, or affixation to outer ear portions, of the left and right ears. In another example, the first and second physiologic sensors are respectively included in two temple-pieces for affixation to the left and right temple regions of the subject.

In some examples, the second physiologic sensor may be included in an implantable medical device, such as the AMD 110 or the implantable device 620 in FIG. 6. Alternatively, the second physiologic sensor may be associated with a lead, such as the lead system 108 coupled to the implantable medical device. The second physiologic sensor may be an implantable accelerometer configured to sense an epicardial or endocardial acceleration (EA) signal $X_I(t)$ from a portion of a heart.

At 840, a composite signal may be generated using the sensed first and second physiologic signals. In an example, the first physiologic signal may be transmitted from the headgear to the implantable device, or an external system such as the external system 125, where the composite signal can be generated. The data transmission may be through a wired or wireless communication link. The composite signal may be a linear or a non-linear combination of the first and second physiologic signals each indicative of heart sounds. In the case that the first and second physiologic signals are sensed by the sensors placed at opposite head locations (e.g., ear canals of left and right ear, or left and right temples), a phase relationship between the physiologic signals may be detected. In an example, the phase relationship may be detected between motion interference components contained in the respective first and second physiologic signals. The motion interference components may be caused by locomotion or other physical activities. The sensed first or second physiologic signal may be filtered to remove or attenuate the respective motion interference component using the detected phase relationship. In an example, the motion interference components of the first and second physiologic signals (e.g., acquired from left and right ear canals, or from left and right temples) is substantially out of phase. The composite signal at 840 may be generated by adding the second physiologic signal and the first physiologic signal to substantially remove or attenuate the motion interference from the first physiologic signal.

At 850, one or more heart sound components, such as S1, S2, S3, or S4, may be detected from the composite heart sound signal, and a heart sound metric may be generated using the detected heart sound components. The heart sound metric may include temporal, statistical, or morphological features of one or more detected heart sound components, or cardiac timing intervals (CTI) between a cardiac electrical even and a mechanical event. In some examples, the implantable medical device may additionally or alternatively detect cardiac electrical signals such as ECG or EGM, and detect timing information of the cardiac depolarizations, such as Q wave, R wave, QRS complex, or localized cardiac depolarization. The timing information of the cardiac depolarizations may be used to define respective detection windows (e.g., S1 detection window or S2 detection window) for detecting the heart sound components from the first physiologic signal that is sensed by the headgear sensor.

The generated heart sounds metric, optionally along with the detected heart sound components, may be provided to one or more of the processes 862 and 864. At 862, the heart sound metric may be output to a user or a process, such as via an output device of the user interface 632. In an example, the heart sound metric may be displayed on a display, including the sensed physiologic signal, patient baseline cardiac characteristics and patient-specific detection criterion, among others. Hard copies of the detection information may be generated. The heart sound metric may be used to trigger an alert, alarm, emergency calls, or other forms of warnings if the heart sound metric satisfies a specified condition (such as falling below a threshold or within a specified range).

At 864, the heart sound metric may be used to detect a cardiac event, such as a worsening heart failure (WHF) event. A WHF event may be detected by comparing the heart sound metric to a detection threshold. In some examples, a composite signal index may be generated using a combination of various signal metrics including the heart sound metric, and a WHF alert may be generated when the composite signal index exceeds a detection threshold. In various examples, the method 800 may include an optional step 866 of delivering a therapy to the patient in response to the detected cardiac event such as the WHF event. Examples of the therapy may include electrostimulation therapy delivered to the heart, a nerve tissue, other target tissue, a cardioversion therapy, a defibrillation therapy, or drug therapy including delivering drug to a tissue or organ. In some examples, an existing therapy or treatment plan may be modified to treat the detected arrhythmia.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for sensing heart sounds in a subject, comprising:
    a first earpiece configured to be positioned at an outer portion of a left ear of the subject and to sense a first physiologic signal therefrom via a first sensor, and a second earpiece configured to be positioned at an outer portion of a right ear of the subject and to sense a second physiologic signal therefrom via a second sensor, the first and second physiologic signals each including mechanical information associated with blood flow in the subject; and
    a processor configured to:
        determine a first motion artifact component from the first physiologic signal and determine a second motion artifact component from the second physiologic signal;
        generate an alert to the subject to re-position at least one of the first or the second earpiece until the first motion artifact component is substantially out of phase relative to the second motion artifact component;
        combine the sensed first and second physiologic signals to remove or attenuate the first and the second motion artifact components representing motion of the subject common to but substantially out of phase between the first and second physiologic signals from the respective first and second sensors at the first and second earpieces at the left and the right ears of the subject, respectively; and
        process the combined signal and generate therefrom a heart sound metric, the heart sound metric including at least one of S1, S2, S3, or S4 heart sound of the subject as received at the first and second earpieces.

2. The system of claim 1, wherein the first earpiece and the second earpiece are each configured to be removably affixed within a portion of an auditory canal of the outer portion of respective ear.

3. The system of claim 1, comprising an implantable device communicatively coupled to the first sensor and the second sensor, the implantable device including the processor.

4. The system of claim 1, wherein one of the first sensor or the second sensor is an accelerometer sensor configured to sense motion, vibration, or displacement conducted through body tissue of the subject.

5. The system of claim 1, wherein to combine the sensed first and second physiologic signals, the processor is configured to generate a linear or non-linear combination of the first and second physiologic signals.

6. The system of claim 1, wherein to combine the sensed first and second physiologic signals, the processor is configured to add the first physiologic signal to the second physiologic signal in a time domain.

7. The system of claim 1, comprising a cardiac event detector configured to detect a worsening heart failure event using the generated heart sound metric.

8. The system of claim 1, wherein to combine the sensed first and second physiologic signals to remove or attenuate the first and the second motion artifact components includes using a filter circuit or a filter bank.

9. A method of sensing heart sounds in a subject using a first earpiece positioned at an outer portion of a left ear of the subject and a second earpiece positioned at an outer portion of a right ear of the subject, the method comprising:

sensing a first physiologic signal via a first sensor included in the first earpiece from the outer portion of the left ear of the subject;

sensing a second physiologic signal via a second sensor included in the second earpiece from the outer portion of the right ear of the subject, wherein the first and second physiologic signals each include mechanical information associated with blood flow in the subject;

via a processor circuit, determining a first motion artifact component from the first physiologic signal and determine a second motion artifact component from the second physiologic signal;

via the processor circuit, generating an alert to the subject to re-position at least one of the first or the second earpiece until the first motion artifact component is substantially out of phase relative to the second motion artifact component;

via the processor circuit, combining the sensed first and second physiologic signals to remove or attenuate the first and the second motion artifact components representing motion of the subject common to but substantially out of phase between the first and second physiologic signals from the respective first and second sensors at the first and second earpieces at the left and the right ears of the subject, respectively; and via the processor circuit, processing the combined signal and generating a heart sound metric including at least one of S1, S2, S3, or S4 heart sound of the subject as received at the first and second earpieces.

10. The method of claim 9, further comprising:

providing an implantable device configured to communicate with the first and second earpieces, the implantable device including the processor circuit;

establishing a communication between the implantable device and the first and second earpieces; and transmitting information including the sensed first and second physiologic signals from the first and second earpieces to the implantable device.

11. The method of claim 9, wherein combining the first and second physiologic signals includes adding the second physiologic signal and the first physiologic signal when the first and the second motion artifact components are substantially out of phase.

12. The method of claim 9, further comprising detecting worsening heart failure using the generated heart sound metric.

13. The method of claim 9, wherein the first and second physiologic signals each include a cardiac, valvular, or arterial activity component, the method further comprising determining a phase relationship between the cardiac, valvular, or arterial activity component of the first physiologic signal and the cardiac, valvular, or arterial activity component of the second physiologic signal, wherein combining the sensed first and second physiologic signals further includes using the determined phase relationship.

14. The method of claim 9, wherein combining the sensed first and second physiologic signals includes generating a linear or non-linear combination of the sensed first and second physiologic signals.

15. A system for sensing heart sounds in a subject, comprising:

a first earpiece configured to be positioned at an outer portion of a left ear of the subject and to sense a first physiologic signal therefrom via a first sensor, and a second earpiece configured to be positioned at an outer portion of a right ear of the subject and to sense a second physiologic signal therefrom via a second sensor, the first and second physiologic signals each including a cardiac, valvular, or arterial activity component that includes mechanical information associated with blood flow in the subject; and a processor configured to:

determine a phase relationship between the cardiac, valvular, or arterial activity component of the first physiologic signal and the cardiac, valvular, or arterial activity component of the second physiologic signal;

combine the sensed first and second physiologic signals based at least one the determined phase relationship to remove or attenuate motion artifact components representing motion of the subject common to but substantially out of phase between the first and second physiologic signals from the respective first and second sensors at the first and second earpieces at the left and the right ears of the subject, respectively; and process the combined signal and generate therefrom a heart sound metric, the heart sound metric including at least one of S1, S2, S3, or S4 heart sound of the subject as received at the first and second earpieces.

16. The system of claim 15, wherein the first earpiece and the second earpiece are each configured to be removably affixed within a portion of an auditory canal of the outer portion of respective ear.

17. The system of claim 15, comprising an implantable device communicatively coupled to the first sensor and the second sensor, the implantable device including the processor.

18. The system of claim 15, wherein one of the first sensor or the second sensor is an accelerometer sensor configured to sense motion, vibration, or displacement conducted through body tissue of the subject.

19. The system of claim 15, wherein to combine the sensed first and second physiologic signals to remove or attenuate the first and the second motion artifact components includes using a filter circuit or a filter bank.

20. The system of claim 15, comprising a cardiac event detector configured to detect a worsening heart failure event using the generated heart sound metric.

* * * * *